(12) United States Patent
Zhao et al.

(10) Patent No.: US 8,282,581 B2
(45) Date of Patent: Oct. 9, 2012

(54) ULTRASOUND TREATMENT CLAMP

(75) Inventors: Chunliang Zhao, Chongqing (CN);
Aihua Mao, Chongqing (CN);
Guangyun Lei, Chongqing (CN)

(73) Assignee: Chongqing Haifu (Hifu) Technology Co., Ltd., Chongqing (CN)

( * ) Notice: Subject to any disclaimer, the term of this patent is extended or adjusted under 35 U.S.C. 154(b) by 1118 days.

(21) Appl. No.: 12/161,219

(22) PCT Filed: Jul. 7, 2006

(86) PCT No.: PCT/CN2006/001716
§ 371 (c)(1),
(2), (4) Date: Jul. 17, 2008

(87) PCT Pub. No.: WO2007/082422
PCT Pub. Date: Jul. 26, 2007

(65) Prior Publication Data
US 2009/0275865 A1 Nov. 5, 2009

(30) Foreign Application Priority Data
Jan. 18, 2006 (CN) .......................... 2006 1 0001632

(51) Int. Cl.
*A61H 1/00* (2006.01)
(52) U.S. Cl. .................... 601/2; 601/1; 601/3; 600/437; 600/439
(58) Field of Classification Search .................. None
See application file for complete search history.

(56) References Cited

U.S. PATENT DOCUMENTS

| | | | |
|---|---|---|---|
| 4,662,068 A | 5/1987 | Polonsky | |
| 4,711,240 A * | 12/1987 | Goldwasser et al. | 606/174 |
| 6,083,159 A | 7/2000 | Driscoll, Jr. et al. | |
| 6,139,561 A | 10/2000 | Shibata et al. | |
| 6,312,426 B1 * | 11/2001 | Goldberg et al. | 606/33 |
| 6,432,067 B1 | 8/2002 | Martin et al. | |
| 6,582,451 B1 * | 6/2003 | Marucci et al. | 606/207 |
| 7,322,995 B2 * | 1/2008 | Buckman et al. | 606/157 |
| 7,473,224 B2 * | 1/2009 | Makin | 600/439 |
| 7,553,284 B2 * | 6/2009 | Vaitekunas | 600/439 |
| 2007/0038115 A1 * | 2/2007 | Quigley et al. | 600/471 |

FOREIGN PATENT DOCUMENTS
| | | |
|---|---|---|
| JP | 2001-37771 | 2/2001 |
| JP | 2002-306503 | 10/2002 |

* cited by examiner

*Primary Examiner* — Long V. Le
*Assistant Examiner* — Bradley Impink
(74) *Attorney, Agent, or Firm* — McDermott Will & Emery LLP

(57) ABSTRACT

The present invention relates to an ultrasound treatment clamp. The ultrasound treatment clamp comprises ultrasound therapy applicators and handles connected to the ultrasound therapy applicators. The handles are clamp-shaped. The two ultrasound therapy applicators with their central axes overlapping each other are mounted face to face on the two clamps of the clamp-shaped handles respectively. A parallel moving mechanism for keeping the two ultrasound therapy applicators in parallel when moving along with clamps is connected between the two clamps. The present invention has a compact structure, a convenient operation, a low treatment cost, a capability of quickly causing a coagulative necrosis of the diseased part. Furthermore, the present invention has an abroad use in treating many kinds of diseases.

15 Claims, 7 Drawing Sheets

ULTRASOUND TREATMENT CLAMP

RELATED APPLICATIONS

This application is the U.S. National Phase under 35 U.S.C. §371 of International Application No. PCT/CN2006/001716, filed on Jul. 17, 2006, which in turn claims the benefit of Chinese Application No. 200610001632.5, filed on Jan. 18, 2006, the disclosures of which Applications are incorporated by reference herein.

TECHNICAL FIELD OF THE INVENTION

The present invention belongs to the technical field of medical instruments, relates to a high-intensity focused ultrasound treatment apparatus, and particularly relates to an ultrasound treatment clamp.

BACKGROUND OF THE INVENTION

Ultrasound, especially high-intensity focused ultrasound has been widely used in medical industry for diagnosis and treatment on a patient. A high-intensity focused ultrasound therapy is to focus the ultrasound on the diseased part, on which high-intensity and continuous ultrasonic energy is formed and thereby instantaneous thermal effect (60° C.~100° C.), cavitation effect, mechanical effect and acoustic chemical effect are produced to destroy the cell membrane and nuclear membrane and coagulate the protein. Therefore, it can selectively cause a coagulative necrosis of the diseased tissue and accordingly deprives the diseased part of capability of proliferation, infiltration and metastasis. Furthermore, the high-intensity focused ultrasound therapy is not only used in tumor resection but also in treatment of other diseases, and it has been approved in clinical uses.

U.S. Pat. Nos. 5,882,302, 5,993,389 and 6,083,159 provide an ultrasound apparatus for surgery in the internal hemostasis by using a high-intensity focused ultrasound. U.S. Pat. Nos. 6,007,499 and 6,432,067 also provide a surgical ultrasound apparatus using a high-intensity focused ultrasound to form narcotic tissue regions before a surgery so as to avoid the bleeding of vasalium when performing surgery. The ultrasound transducer of this apparatus generates the focused ultrasound and emits continuously to a certain point of the diseased part. The treatment depth of the focal point can be varied by changing the positions of the ultrasound transducer.

The ultrasound apparatuses disclosed by the above-mentioned US patents can, to some extent, provide a hemostasis in the resection of tissue having a highly vascularized constitution, but there are some limits on the use of these apparatuses. Firstly, the operator needs to continuously move the large-sized ultrasound transducer by hand in the same angle according to different surgical incisions, so the operation procedure is very complex and also it is liable to cause mishandlings. Secondly, when the tissue to be treated is soft and incompact, the pressure generated by the apparatuses as mentioned above on the target tissue is not enough, so it is impossible to control the target tissue effectively, and if the target tissue can not be controlled, the ultrasonic energy can not arrive at the target tissue and the expected hemostasis can not be achieved. Thirdly, because the ultrasound apparatuses mentioned above can form only one focal point within the diseased part and usually the ultrasonic energy is attenuated on the acoustic path, it takes a lot of time to cause a coagulative necrosis of the relatively thick tissue (for example, the liver and spleen) during treatment and accordingly the cost is increased.

SUMMARY OF THE INVENTION

Aiming at the disadvantages in the prior art as mentioned above, the technical problem is solved in the present invention by providing an ultrasound treatment clamp with a compact structure, a convenient operation, a low treatment cost, a capability of quickly causing a coagulative necrosis of the diseased part to avoid excessive lose of blood of a patient, and an abroad use.

The technical solution to solve the technical problem in the present invention is as follows: the ultrasound treatment clamp comprises ultrasound therapy applicators and handles connected to the ultrasound therapy applicators. The handles are clamp-shaped. Two ultrasound therapy applicators with their central axes overlapping each other are mounted face to face on the two clamps of the clamp-shaped handles respectively. A parallel moving mechanism for keeping two ultrasound therapy applicators in parallel when moving along with the clamps is connected between two clamps.

Said ultrasound therapy applicator further comprises connection tubes, one end of which is connected to the ultrasound therapy applicator and the other end is connected to the clamp of the clamp-shaped handle. Said parallel moving mechanism is connected between the two opposite connection tubes.

In the practical use, because the sizes and shapes of the target tissue are different, the joint can be connected to the ultrasound therapy applicator by a rotating joint. Because the rotating joint can rotate freely, the ultrasound therapy applicator can rotate freely on the rotating joint, that is, it can focus the ultrasound transversely or longitudinally.

The parallel moving mechanism enables the focal regions of two ultrasound therapy applicators to be in the same straight line in any opening degree of the treatment clamp, i.e. it can keep the central axes of two applicators overlapping each other all along. Thus, when high-intensity ultrasound energy is needed for a treatment, the ultrasound energy can be accumulated, i.e. two applicators apply ultrasound energy simultaneously to the same diseased part, so the therapeutic effects can be enhanced. During treatment, the time to cause a coagulative necrosis of the thick diseased tissue (for example, the liver or spleen) by using the applicators in the present invention is greatly shorter than that by using the ultrasound applicators in the prior art, so the treatment cost is saved. Meanwhile, the ultrasonic energy is emitted from more than one ultrasound applicator, so other internal organs will not be injured.

Said parallel moving mechanism may comprise a telescoping mechanism in a parallelogram formed by a plurality of link blocks hinged with each other. There is a sliding sleeve on the connection tube for sliding back and forth. The link block at one corner of the outer part of the parallel moving mechanism is hinged with the sliding sleeve and the link block at the other corner of the outer part is fixed on the clamp.

Said parallel moving mechanism may be telescopic pipe components comprising big hollow pipes and small hollow pipes in different diameters, said small hollow pipes are encased in the big ones and can extend and slide.

Said ultrasound therapy applicator comprises an ultrasound transducer and a fluid container. The ultrasound transducer is placed in the fluid container and an acoustic transparent membrane is fixed at the open part of the container by an airtight device.

Wherein, said fluid is preferably the degassed water. Said ultrasound transducer can adopt focusing or non-focusing ultrasound transducers according to the practical needs. Thus, the apparatus of the present invention can be used widely to treat other diseases, such as tumor, skin diseases and etc.

A bracket is provided in said fluid container and the ultrasound transducer is placed on the bracket. Preferably, a focal distance adjusting device is provided on the fluid container further. One end of said focal distance adjusting device extending into the fluid container is connected to the bracket.

Said focal distance adjusting device may include a screw connected to the bracket, a seal ring and a seal nut covered on the screw, an adjusting knob on the seal nut and a fixing bolt on the adjusting knob. The seal ring clings to the outside wall of the fluid container.

A slot for mounting an ultrasound therapy guiding assembly is provided in said ultrasound transducer. Said guiding assembly may be a semiconductor light device or a B-mode ultrasound probe. The semiconductor lighting device is fixed in the slot and is used to guide the ultrasound transducer to perform an accurate treatment. Before the treatment, according to the position of light beams emitted from the semiconductor lighting device, the operator can locate the ultrasound applicator to the surface of the target tissue, and the intersection point of the focal point/line of the therapy applicator and light beams of the diode is confirmed. Also an ultrasonic imaging apparatus such as a B-mode ultrasound probe can be fixed in that slot to image the target tissue and guide the ultrasound therapy.

In order to avoid a heat injury to the target tissue, said ultrasound therapy applicator further comprises a temperature sensor fixed on the opposite side of said two ultrasound transducers (i.e. the side of the target tissue clamped by the ultrasound transducers). Because a membrane type temperature sensor is light and thin, the temperature sensor is preferably the membrane type temperature sensor.

A locker for fixing the handles may be provided between the two handles. Thus, after the parallel moving mechanism driven by the handles extends to the predetermined position, the locker can be used to fix the current position of two handles to make convenience for the treatment.

In the present invention, before the resection of tissue having a highly vascularized constitution (for example, spleen, kidney, liver and etc.), the high-intensity focused ultrasound is applied to cause a coagulative necrosis area between the area to be resected and the area to be reserved. Therefore, during the resection of tissues such as liver, the coagulative necrosis area is taken as the area to be resected by a surgical knife. The structure of the treatment clamp in the present invention offers an easy manual operation by an operator. Through an operation of two clamps, two ultrasound therapy applicators can firmly clamp the target tissue. Thus, the target tissue can be controlled effectively. The resection will not cause excessive blood loss, so the possibility of blood transfusion is reduced and also the occurrence of complications after surgery is decreased. Moreover, the two ultrasound therapy applicators of the present invention can work simultaneously, by which the time to cause a coagulative necrosis of the incisions is shortened and the effect of the hemostasis of the target tissue is ensured.

The present invention also has other advantages such as possessing a compact structure, low treatment cost and abroad uses (the ultrasound transducer with different specifications can be chosen according to different needs).

Figure 1:
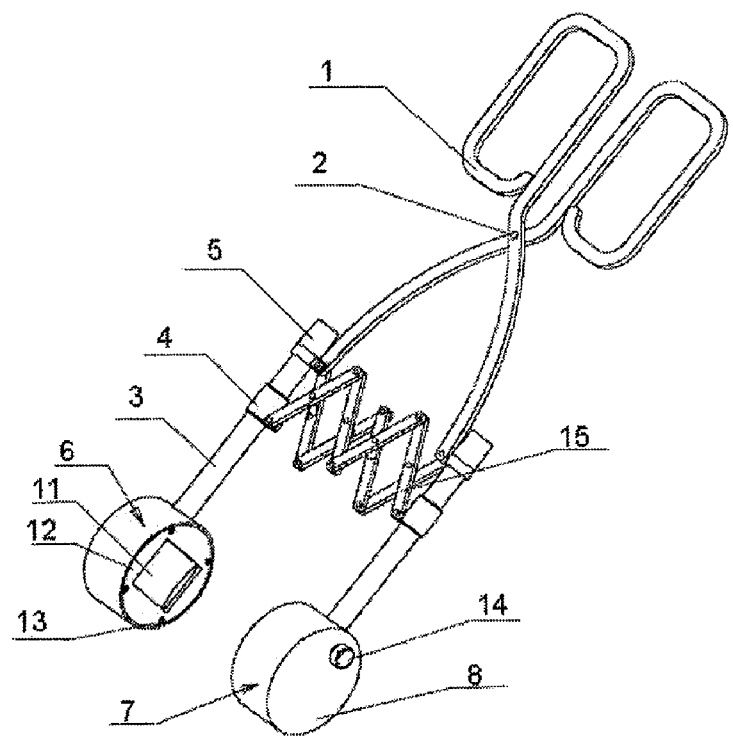
FIG. 1 is a structural schematic diagram of the embodiment 1 of the present invention.

Wherein: 1-Handle 2-Pin 3-Connection tube 4-Sliding sleeve 5-Joint 6-First therapy applicator 7-Second therapy applicator 8-Fluid container 9-Ultrasound transducer 10-Bracket 11-Acoustic transparent membrane 12-Cover board 13-Bolt 14-Focal distance adjusting device 141-Screw 142-Seal ring 143-Seal nut 144-Adjusting knob 145-Fixing bolt 15-Link block 16-Slot 17-Semiconductor light device 18-B-mode ultrasound probe 19-Temperature sensor 20-Telescopic pipe components 21-Single telescopic pipe 22-Rotating joint 23-Locker 24-Small multiple outlets hose 25-Mainframe control system 251-Display 252-Operation knob 253-Control unit 254-Water pump 255-Water tank 256-Truckle 257-Signal wire 258-Return pipe 259-Inlet water pipe 26-Big multiple outlets hose

DESCRIPTION OF THE PREFERRED EMBODIMENTS

As shown in FIGS. 1 to 12, the present invention comprises a handle 1, two ultrasound therapy applicators arranged face to face and a parallel moving mechanism for keeping two ultrasound therapy applicators in parallel when moving along with the clamps. The handle 1 is clamp-shaped. Two ultrasound therapy applicators are mounted face to face on two front ends of the clamp-shaped handle 1 respectively and the central axes of two applicators overlap each other.

The ultrasound therapy applicator comprises an ultrasound transducer 9 and a fluid container 8. The ultrasound transducer 9 is placed in the fluid container 8. An acoustic transparent membrane 11 is fixed on the open part of the fluid container 8 by an airtight device.

The ultrasound transducer 9 can adopt focusing or non-focusing ultrasound transducers. The focusing transducer is mainly used for hemostasis during operations and for treating deep-bedded diseased part in the tissue, for example, hepatic carcinoma, bone carcinoma, deep-bedded myosarcoma and etc. The focusing ultrasound transducer may be a single circular piezoelectric ceramic crystal with a lens for focusing, or a single spherical surface or a single arc surface piezoelectric ceramic crystal, or a piezoelectric ceramic crystal array comprising a plurality of piezoelectric ceramic crystals with the same size or different sizes, the driving mode of which may be a single-channel signal one or a multi-channel signal one in phase control. The non-focusing ultrasound transducer is mainly used for skin diseases and the diseased parts in the upper surface of skin. The non-focusing ultrasound transducer may be a single flat piezoelectric ceramic crystal, or a piezoelectric ceramic crystal array comprising a plurality of flat piezoelectric ceramic crystals with the same size or different sizes, the driving mode of which may be a single-channel signal one or a multi-channel signal one in phase control.

Also a slot 16 is provided in said ultrasound transducer 9, and a semiconductor lighting device or a B-mode ultrasound probe for guiding an ultrasound therapy can be fixed in the slot 16. A locker for fixing the handles may be provided between the two handles.

Preferably, said ultrasound therapy applicator further comprises a temperature sensor 19 fixed on the side of the target tissue clamped by the two ultrasound transducers.

The ultrasound therapy applicator further comprises a connection tube 3, one end of which is connected to the fluid container 8 and the other end is connected to the clamp of the clamp-shaped handle 1 through a joint 5. Said parallel moving mechanism is connected between the two opposite connection tubes 3. There are passages for fluid and electrical signals at one end where the connection tube 3 and the joint 5 are connected. Said passages for fluid and electrical signals are both connected to the ultrasound therapy applicator.

The present invention will be further explained below with reference to the preferred embodiments and accompanying drawings.

The flowing embodiments are unrestrictive embodiments of the present invention.

Embodiment 1

As shown in FIG. 1, the present invention comprises a handle 1, ultrasound therapy applicators and a parallel moving mechanism. Wherein, the handle 1 is clamp-shaped and two clamps of the handle 1 are connected by a pin 2. There are two ultrasound therapy applicators, which respectively are a first therapy applicator 6 and a second therapy applicator 7 mounted respectively face to face on two front ends of the clamp-shaped handle 1 and the central axes of the two applicators overlap each other.

Each of the first therapy applicator 6 and the second therapy applicator 7 comprises a fluid container 8, an ultrasound transducer 9, an acoustic transparent membrane 11, a cover board 12 and a connection tube 3. The connection tube 3 is connected to the ultrasound transducer 9 at one end and is connected to the clamp of the handle 1 at the other end. The ultrasound transducer 9 is placed in the fluid container 8. The acoustic transparent membrane 11 is fixed on the open part of the fluid container 8 through an airtight device, i.e. the cover board 12. The fluid container 8 is full of degassed water. In this embodiment, the fluid is the purified water. The ultrasound transducer adopts a single spherical surface piezoelectric ceramic crystal which can focus and is used to treat a deep-bedded diseased part with a small size.

Figure 2:
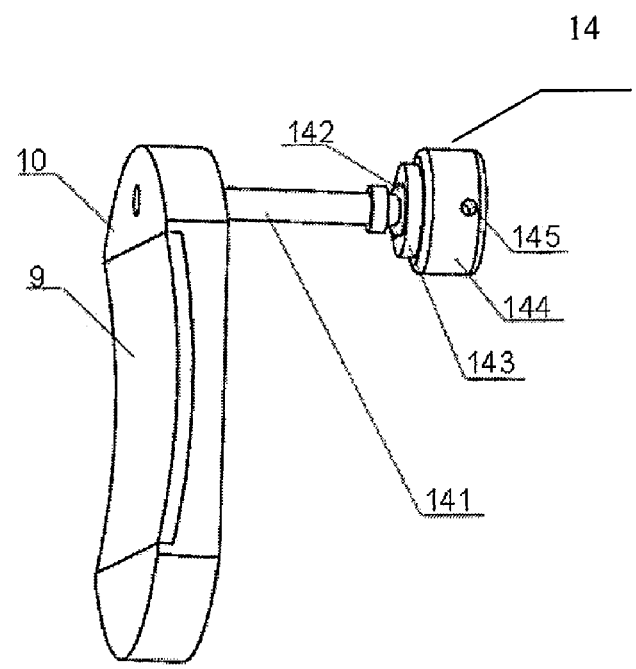
FIG. 2 is a structural schematic diagram of the ultrasound transducer 9 and the focal distance adjusting device 14 in embodiment 1 of the present invention.

As shown in FIG. 2, the ultrasound transducer 9 is placed on a bracket 10. A focal distance adjusting device 14 of the ultrasound transducer 9 is connected to the bracket 10. The focal distance adjusting device 14 is placed on the fluid container 8.

The focal distance adjusting device 14 includes a screw 141, a seal ring 142, a seal nut 143, an adjusting knob 144 and a fixing bolt 145. The end with a lug boss of the screw 141 is connected to the bracket 10 by thread connection and the other end of the screw 141 goes through the fluid container 8 and is connected to the seal nut 143. The seal nut 143 is connected to the adjusting knob 144. The adjusting knob 144 is fixed by the fixing bolt 145. In order to ensure a seal, the seal ring 142 is installed outside where the screw 141 goes through the external wall of the fluid container 8. When rotating the adjusting knob 144, the bracket 10 moves back and forth under the drive of the screw 141 and accordingly the ultrasound transducer 9 placed on the bracket 10 moves back and forth. This kind of ultrasound transducer with the focal distance adjusting device can satisfy the different treatment depths of the diseased part if the tissue has the same thickness.

The ultrasound transducers 9 in the first therapy applicator 6 and the second therapy applicator 7 can have the same frequency or different frequencies and the two ultrasound transducers are driven respectively by two sets of driving devices. According to the practical conditions, the treatment can use only one applicator or two applicators simultaneously.

In order to ensure two ultrasound therapy applicators keeping in parallel in any opening degree of the clamps of the ultrasound treatment clamp of the present embodiment, that is, to ensure the central axes of two applicators being in the same line at any time, the parallel moving mechanism is provided between two clamps of the handle 1.

There are many methods to realize the parallel moving mechanism. As shown in FIG. 1, a parallelogram telescopic mechanism is adopted in this embodiment. Because a parallelogram always keeps a parallelogram in despite of how the acmes move, i.e. the opposite sides of the parallelogram keep in parallel at any time. This parallel moving mechanism is connected between the two opposite connection tubes 3, comprising a plurality of link blocks 15 hinged with each other by pins. The link block 15 at one corner of outermost end of the parallel moving mechanism is hinged with a sliding sleeve 4 which is on the connection tube 3 and may slide back and forth, and the link block 15 at the other corner of the outermost end of the parallel moving mechanism is fixed on the clamp. Wherein, the sliding sleeve 4 is an essential part to enable the parallel moving mechanism to extend freely under an external force.

Because the first therapy applicator 6 and the second therapy applicator 7 are respectively fixed on the two opposite connection tubes 3, both the two connection tubes 3 are always keeping in parallel whatever opening degrees the clamps of the handle 1 are in. Thus, the first therapy applicator 6 and the second therapy applicator 7 can always move in parallel. Since the clamps are hinged with the joints 5 connected to the ultrasound therapy applicators, the opening and closing of the handle 1 form a power supply for the movement in parallel of the two ultrasound therapy applicators.

Figure 3:
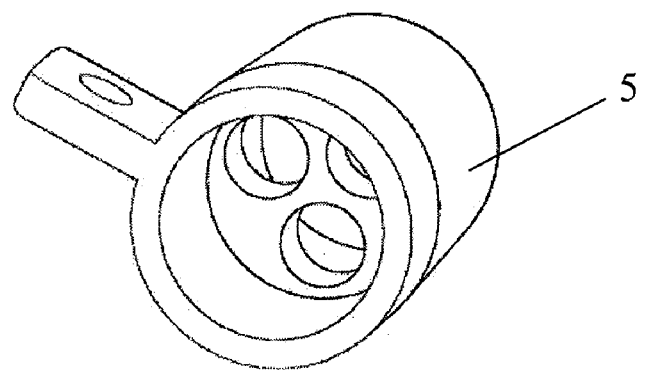
FIG. 3 is a structural schematic diagram of the joint 5 in embodiment 1 of the present invention.

As shown in FIG. 1, the connection tube 3 goes through the side wall of the fluid container 8 and is connected to the fluid container 8 rigidly. The other end of the connection tube 3 is connected to the clamp of the handle 1 through the joint 5. As shown in FIG. 3, there are three passages in the joint 5 and all passages here are connected to the ultrasound therapy applicator and they are respectively used as the inlet water channel, the return channel and the channel for electrical signals of the ultrasound therapy applicator 9. Therefore, the joint 5 is a support for the sliding sleeve 4 as well as channels for circuits and water of the present invention. In this embodiment, both the inlet water channel and the return channel are connected to the fluid container 8. The purified water in the fluid container 8 can be used as an ultrasound coupling medium as well as a cooling liquid for the ultrasound transducer 9, by which the heat produced by the ultrasound transducer 9 during treatment can be removed away quickly.

In this embodiment, all the moving joints of the treatment clamp adopt a pin 2 connection. The purpose of adopting a pin connection is to ensure that there is only one-dimension rotation at the moving joint and the moving in other dimensions is limited, therefore, the twist, vibration and etc. will not be produced in the present invention so that the ultrasound therapy applicators keep their balance all the time when the clamps open or close.

Figure 14:
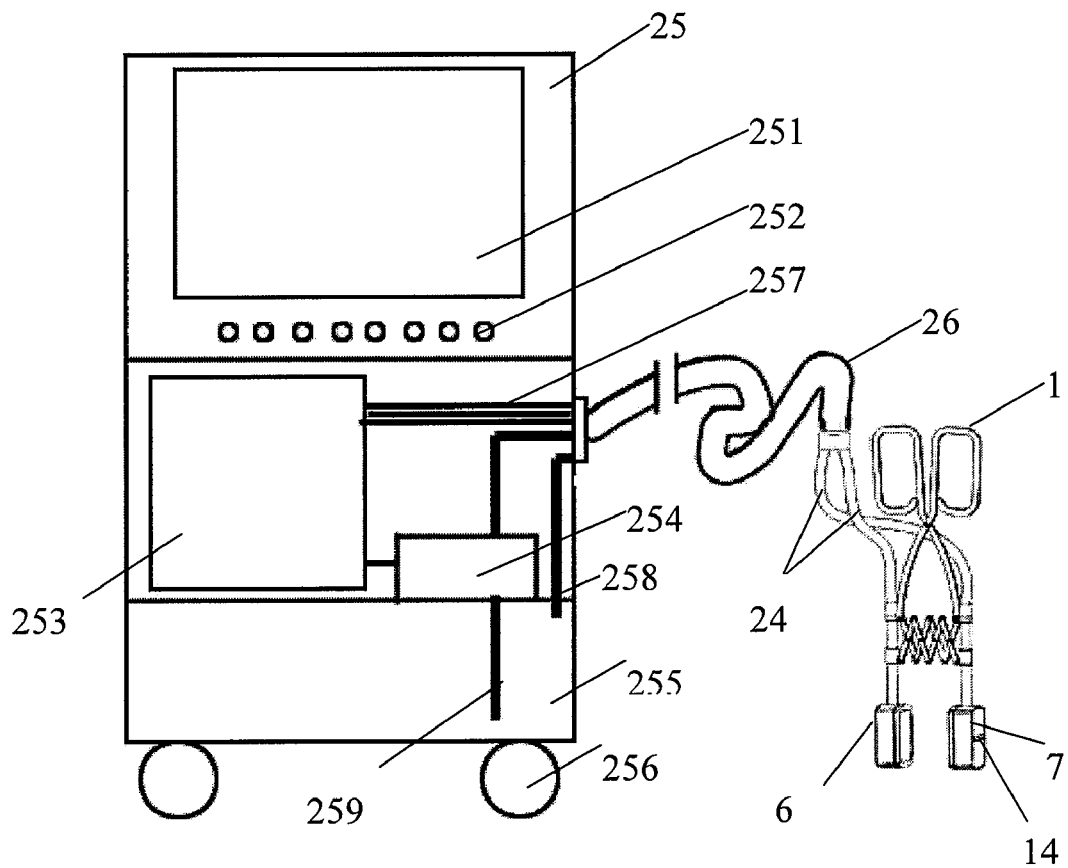
FIG. 14 is a structural schematic diagram of the combined use of the embodiments of the present invention and the mainframe control system 25.

As shown in FIG. 14, the ultrasound treatment clamp of the present embodiment can be used to combine with an external mainframe control system 25. Two small multiple outlets hoses 24 are connected respectively to two joints 5. Each small multiple outlets hose 24 has three passages connected to the three passages of the joint 5. Then, the two small multiple outlets hoses 24 are connected to a big multiple outlets hose 26 through a connector. There are passages in the big multiple outlets hose 26 communicated with the passages of two small multiple outlets hoses 24. The big multiple outlets hose 26 is connected to the mainframe control system 25.

As shown in FIG. 14, in the mainframe control system 25, signal wires 257 are connected to a control unit 253 for providing electrical signals to the ultrasound transducer 9. A water pump 254 is placed on a water tank 255 and is connected to the control unit 253. Under the control of the control unit 253, the purified water in the water tank 255 can enter into a inlet water pipe 259. The inlet water pipe 259 is connected to the inlet water passage of the big multiple outlets hose 26 and the purified water eventually returns to the water tank 255 through a return pipe 258.

As shown in FIG. 14, when the treatment clamp of the present embodiment is used, firstly, push truckles 256 to enable the mainframe control system 25 to be close to the target tissue. The number of the ultrasound therapy applicators to be involved in the treatment has to be determined according to surgical requirements. For example, the two ultrasound therapy applicators can be selected to be used at the same time during treatment, then the operation of the handle 1 enables two applicators to clamp the target tissue tightly. The focal distance of the ultrasound transducer 9 is adjusted by the focal distance adjusting device 14. In the three passages in the joint 5, under the control of the control unit 253, a certain set of the signal wires 257 provides the electric driving signals respectively to the two ultrasound transducers 9. Meanwhile, the purified water serving as ultrasound coupling medium and cooling medium of the ultrasound transducer 9 is inputted into the fluid container 8 through the inlet water pipe 259. In order to make the best use of the water, the purified water eventually returns through the return pipe 258. When the parallel moving mechanism extends under the drive of the handle 1, the two applicators always keep in parallel. The ultrasound transducer 9 emits ultrasound energy and eventually forms a coagulative necrosis area within the target tissue. If the present invention is used for hemostasis, the focused ultrasound is applied to cause a coagulative necrosis area between the area to be resected and the area to be reserved. The tissue necrosis occurs in this coagulative necrosis area and the blood is coagulated. When the doctor resects the diseased part with a surgical knife (for example, the resection of liver tissue and etc.), the resection will not cause excessive blood loss and the possibility of blood transfusion is reduced and also the occurrence of complications after surgery is decreased. If the diseased part is the tumors to be treated, eventually the present invention deprives the diseased part of capability of proliferation, infiltration and metastasis.

Embodiment 2

Figure 4:
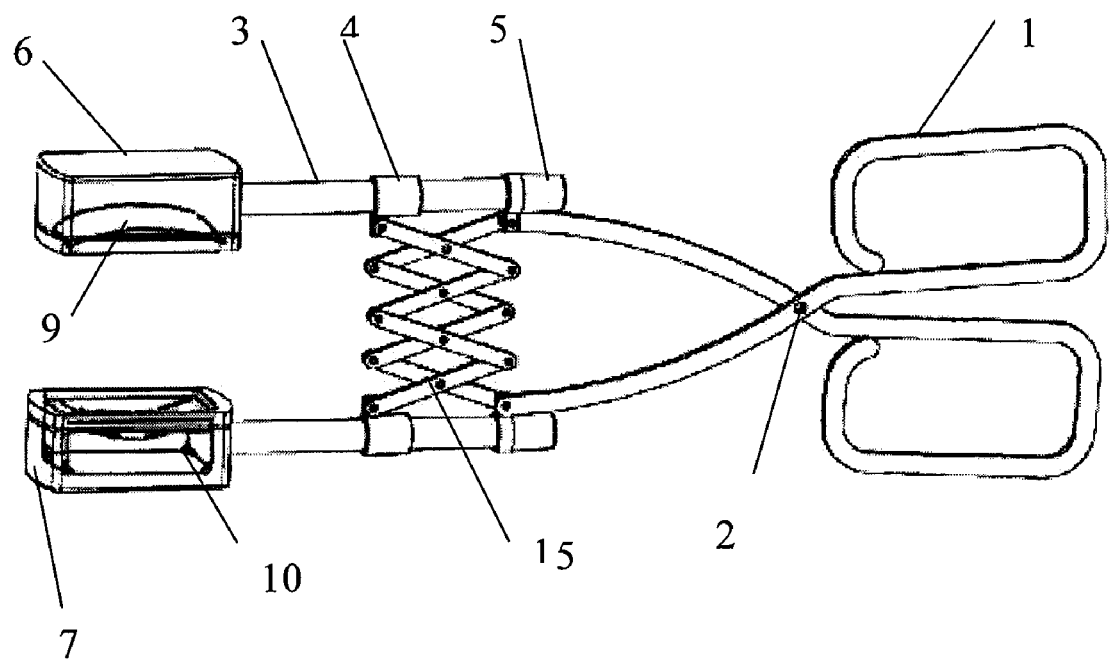
FIG. 4 is a structural schematic diagram of the embodiment 2 of the present invention.

As shown in FIG. 4, the main differences between the present embodiment and the embodiment 1 are as follows: the ultrasound transducers in the present embodiment adopt focusing single arc surface piezoelectric ceramic crystals. This kind of ultrasound transducers is mainly used for hemostasis during surgery and treating the deep-bedded and big-sized diseased parts. Meanwhile, in this embodiment, the two ultrasound therapy applicators have no focal distance adjusting device 14 provided thereon, therefore, the shape of the bracket 10 of the ultrasound transducer 9 is different from that in the embodiment 1. In this embodiment, there is a support leg on the bracket 10 and the support leg is fixed in the ultrasound therapy applicator to make the bracket more firm and steady.

The other structures and the using methods of the present embodiment are the same as those in the embodiment 1.

Embodiment 3

Figure 5:
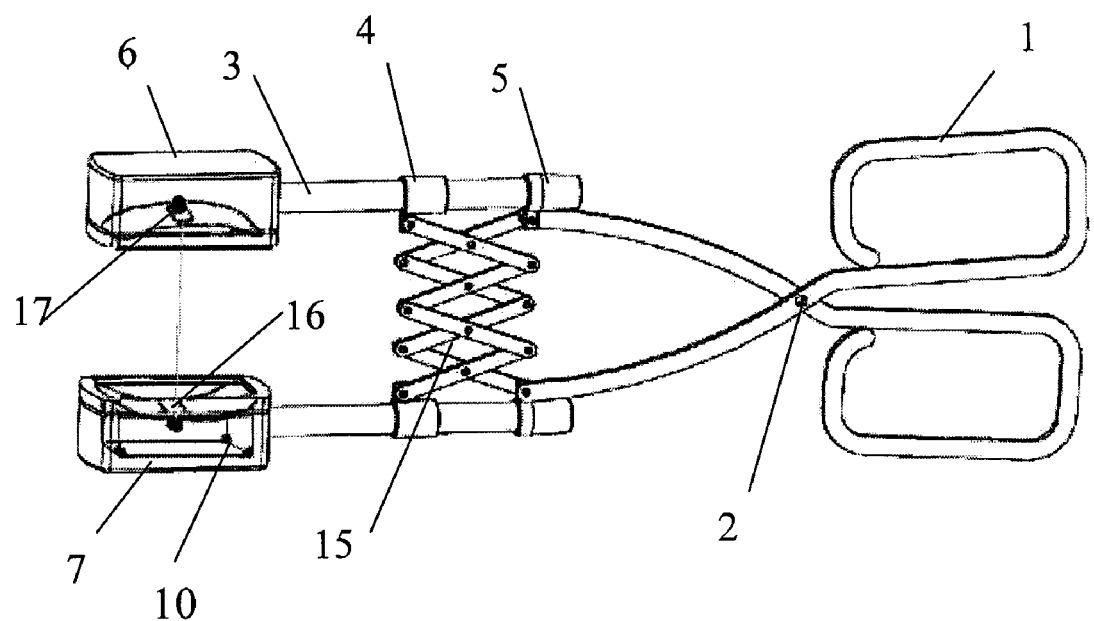
FIG. 5 is a structural schematic diagram of the embodiment 3 of the present invention.

As shown in FIG. 5, in this embodiment, slots 16 are provided in the two ultrasound transducers 9. The semiconductor lighting device 17 are fixed in the slots 16 through bonding for guiding the ultrasound transducer 9 to perform a precise treatment. Before treatment, according to the position of light beams emitted from the semiconductor lighting device 17, the operator can locate the ultrasound applicator on the surface of the target tissue, and the intersection point of the focusing area of the therapy applicator and the position of light beams of the semiconductor lighting device 17 is confirmed so that a precise treatment can be performed.

In this embodiment, the ultrasound transducer 9 adopts a piezoelectric ceramic crystal array comprising of multiple piezoelectric ceramic crystals with the same size or different sizes. The driving mode of this array is a multi-channel signal one in phase control, thus, the operator may drive the ultrasound transducer 9 according to the actual conditions such as the depth of the diseased part so that the focal point can be more precise and the ultrasound energy is more appropriate.

When the ultrasound treatment clamp of the present invention is used to combine with the mainframe control system 25, one set of the signal wires 257 provides the electric driving signals respectively to the two ultrasound transducers 9. The other set of the signal wires 257 provides the electric driving signals respectively to the two semiconductor lighting devices 17.

The other structures and the using methods of the present embodiment are the same as those in the embodiment 2.

Embodiment 4

Figure 6:
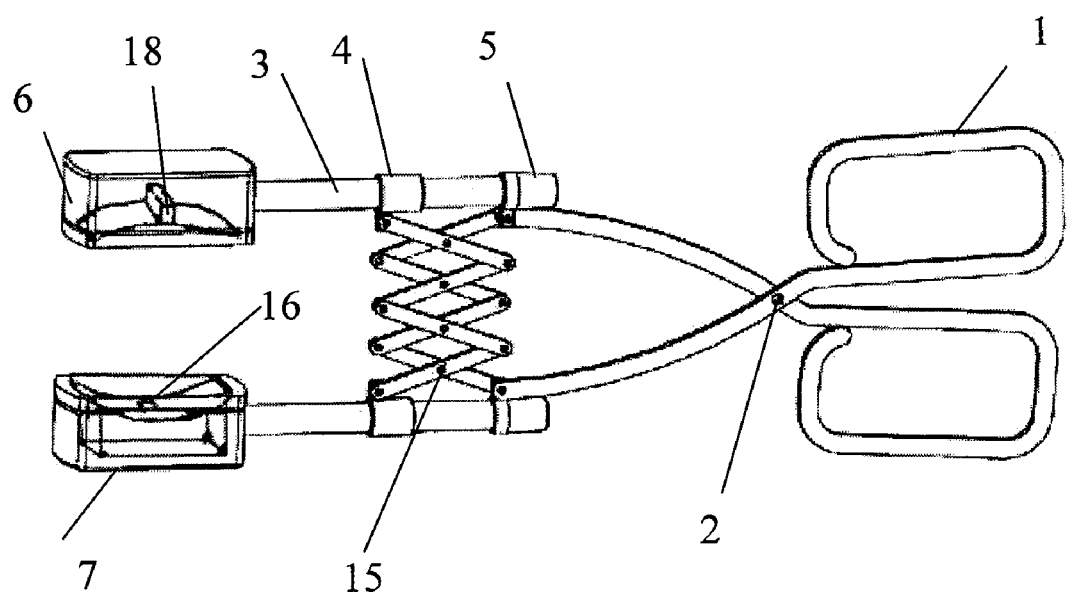
FIG. 6 is a structural schematic diagram of the embodiment 4 of the present invention.

As shown in FIG. 6, a slot 16 is provided in the ultrasound transducer 9. An ultrasound imaging apparatus is fixed in the slot 16. In this embodiment, the ultrasound imaging apparatus adopts B-mode ultrasound probe 18 to image the target tissue and to guide the treatment carried out by the ultrasound treatment clamp of the present invention. The B-mode ultrasound probe 18 can be mounted in any slot 16 of the first therapy applicator 6 and the second therapy applicator 7. In this embodiment, the B-mode ultrasound probe 18 is mounted in the slot 16 of the first therapy applicator 6.

When the ultrasound treatment clamp is used to combine with the mainframe control system 25, the B-mode ultrasound probe 18 is used to image the target tissue and the target tissue is treated on the basis of imaging results.

The other structures and the using methods of the present embodiment are the same as those in the embodiment 2.

Embodiment 5

Figure 7:
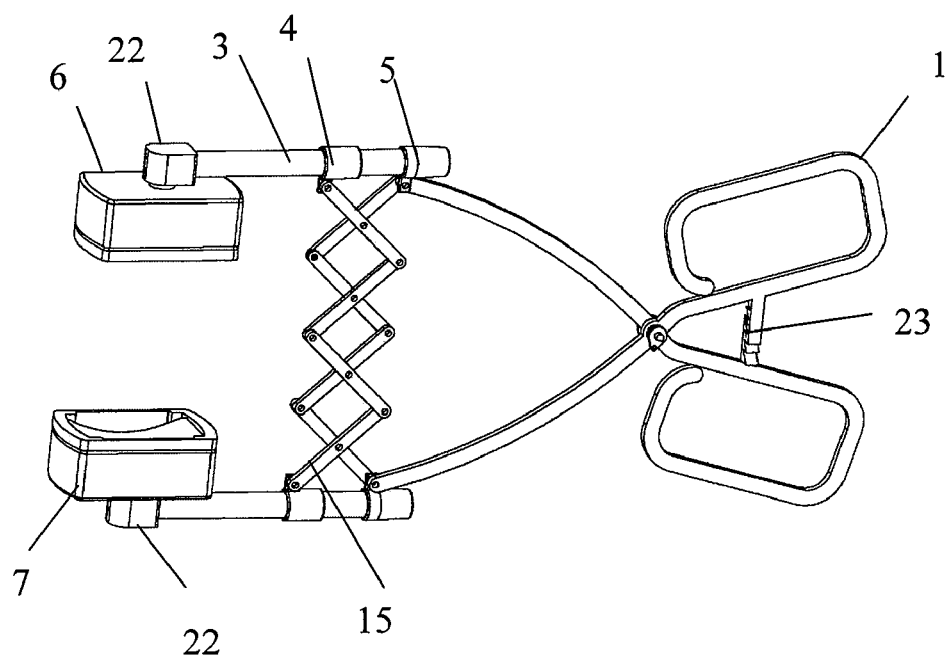
FIG. 7 is a structural schematic diagram of the embodiment 5 of the present invention.

As shown in FIG. 7, in the actual use, the required focusing modes of the ultrasound transducers are different because of different sizes and shapes of the target tissue. There is a rotating joint 22 between the joint 5 and the first therapy applicator 6 or the second therapy applicator 7, which can rotate 90°. The first therapy applicator 6 or the second therapy applicator 7 can rotate freely on the rotating joint 22, i.e. it can focus the ultrasound transversely or longitudinally.

Meanwhile, a locker 23 is added to the handles 1. When the parallel moving mechanism extends under the drive of the handles 1 to the appropriate position, the locker 23 can be used to fix the position of two handles 1.

The other structures and the using methods of the present embodiment are the same as those in the embodiment 2.

Embodiment 6

Figure 8:
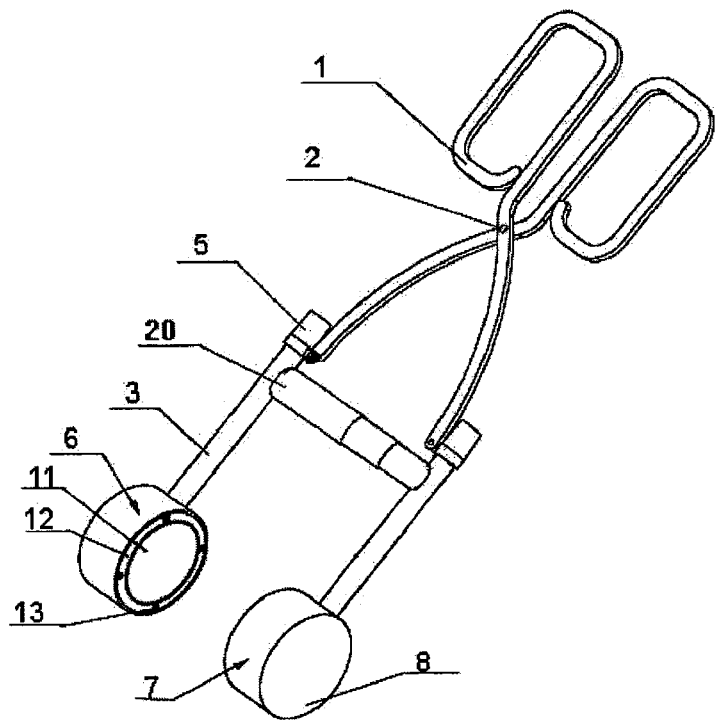
FIG. 8 is a structural schematic diagram of the embodiment 6 of the present invention.
Figure 9:
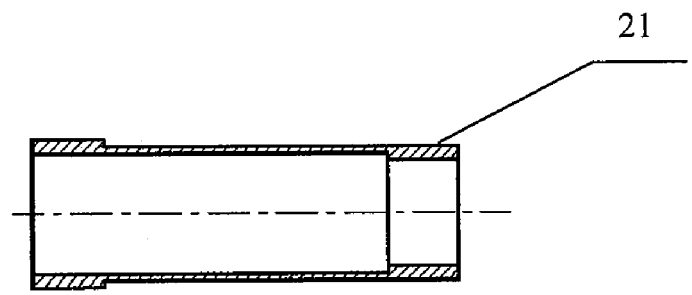
FIG. 9 is a structural schematic diagram of the single telescopic pipe 21 in embodiment 6 of the present invention.

As shown in FIG. 8, the parallel moving mechanism of the present embodiment may adopt the telescopic pipe structure, i.e. telescopic pipe components 20. The telescopic pipe components 20 comprise hollow pipes with different diameters mounted together. A small hollow pipe which can slide and extend freely is mounted in a big one (the same as the principle of telescopic antenna). FIG. 9 is a structural schematic diagram of a single telescopic pipe 21. Each hollow pipe has a limiting lug boss on it so that the small hollow pipe will not be drawn out of the big hollow pipe outside during extending. According to treatment requirements, multiple hollow pipes with different diameters can be provided. In order to ensure the free sliding and extending, the telescopic pipe components 20 consist of at least two single telescopic pipes 21 with different diameters mounted together. Three single telescopic pipes are adopted in this embodiment.

Figure 10:
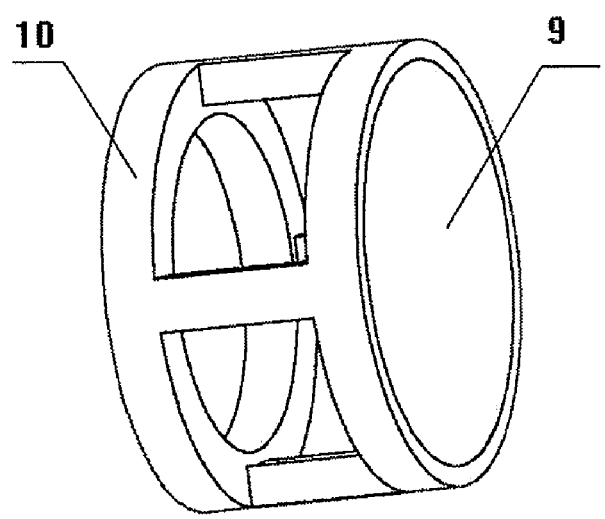
FIG. 10 is a structural schematic diagram of the bracket 10 in the ultrasound therapy applicator and the ultrasound transducer 9 thereon in embodiment 6 of the present invention.

In this embodiment, the ultrasound transducer 9 adopts non-focusing circular piezoelectric ceramic crystals for skin diseases, the diseased parts in the upper surface of skin and etc. As shown in FIG. 10, the ultrasound transducer 9 is fixed on the bracket 10. Because the ultrasound transducer 9 is round-shaped, the shape of the two opposite ultrasound therapy applicators is also a round one. The first therapy applicator 6 and the second therapy applicator 7 have no focal distance adjusting device 14 provided thereon, so the shape of the bracket 10 is different from that in the embodiment 1. There is a support leg on the bracket 10 in this embodiment and the support leg is fixed in the ultrasound therapy applicator to enable the bracket more firm and steady.

The other structures and the using methods of the present embodiment are the same as those in the embodiment 1.

In this embodiment, the first therapy applicator 6 and the second therapy applicator 7 are respectively fixed on two front ends of the two clamps of the handle 1 by the joints 5. The two ends of the telescopic pipe components 20 are connected respectively to the two opposite connection tubes 3. When the telescopic pipe components 20 extend under the drive of the handle 1, the first ultrasound therapy applicator 6 and the second ultrasound therapy applicator 7 keep moving in parallel all the time.

Embodiment 7

Figure 11:
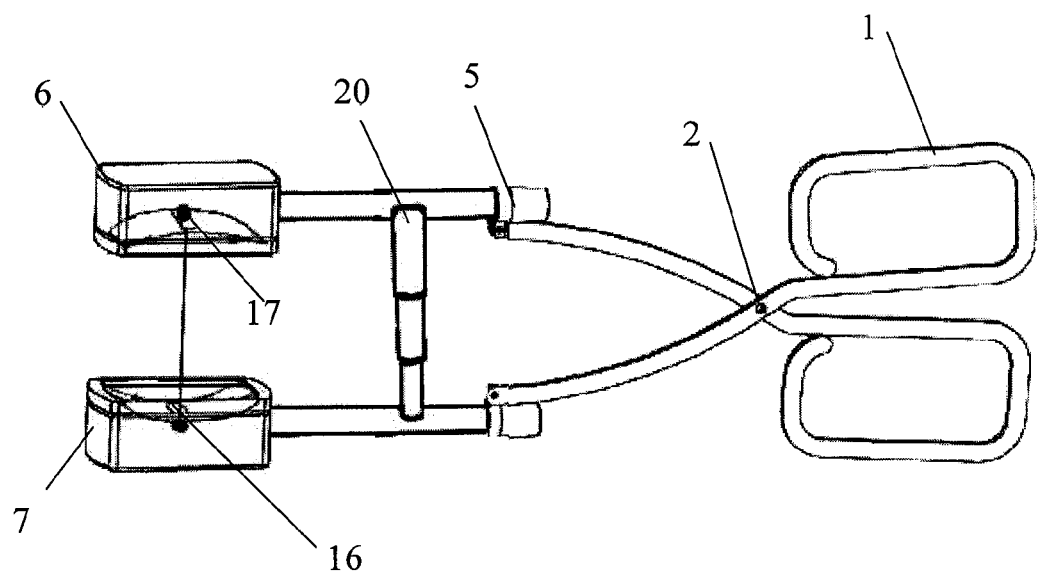
FIG. 11 is a structural schematic diagram of the embodiment 7 of the present invention.

As shown in FIG. 11, except that the parallel moving mechanism in this embodiment adopts telescopic pipe components 20, the other structures and the using methods of the present embodiment are the same as those in the embodiment 3.

Embodiment 8

Figure 12:
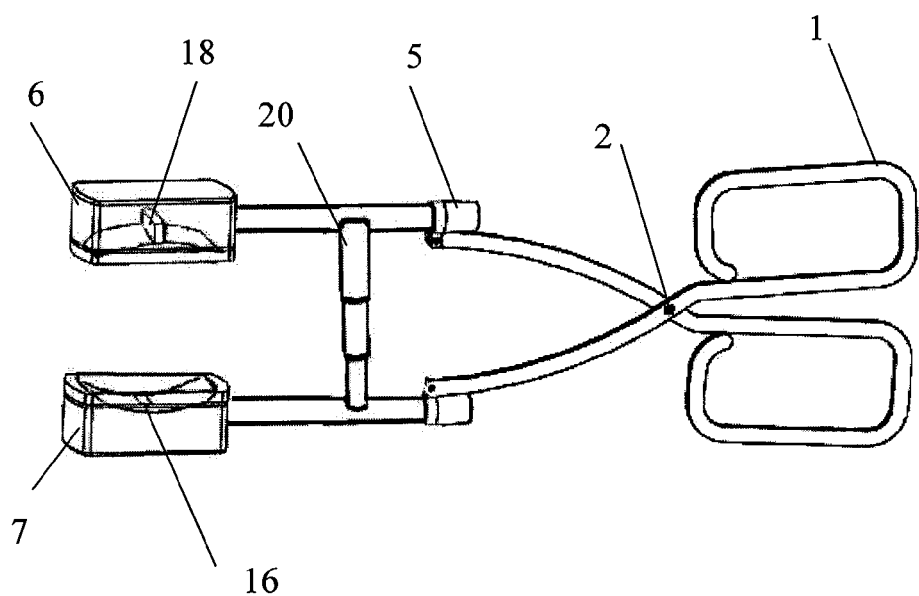
FIG. 12 is a structural schematic diagram of the embodiment 8 of the present invention.

As shown in FIG. 12, except that the parallel moving mechanism in this embodiment adopts telescopic pipe components 20, the other structures and the using methods of the present embodiment are the same as those in the embodiment 4.

Embodiment 9

Figure 13:
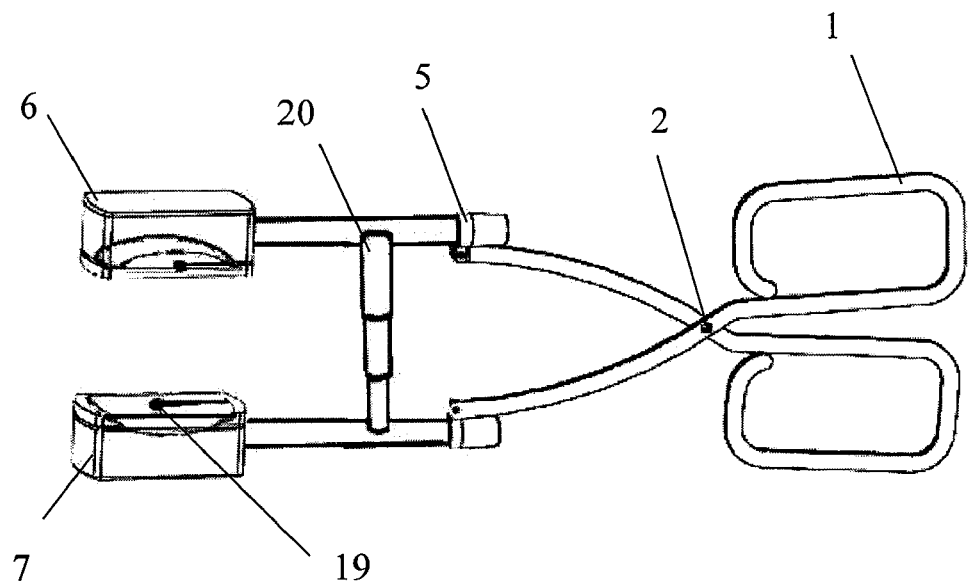
FIG. 13 is a structural schematic diagram of the embodiment 9 of the present invention.

As shown in FIG. 13, the parallel moving mechanism in this embodiment adopts telescopic pipe components 20. Additionally, In order to avoid a heat injury to the target tissue, the first therapy applicator 6 and the second therapy applicator 7 comprise temperature sensors 19, which are fixed on the side of the target tissue clamped by the two ultrasound transducers 9. Because a membrane type temperature sensor is light and thin, the temperature sensor in this embodiment adopts the membrane type temperature sensor.

The other structures and the using methods of the present embodiment are the same as those in the embodiment 2.

As shown in FIG. 14, when the ultrasound treatment clamp of the present embodiment is used combined with the mainframe control system 25, one set of signal wires 257 provides the electric driving signals respectively to the two ultrasound transducers 9. The other set of signal wires 257 provides the temperature monitoring signals to the temperature sensor 19. After the temperature detected is processed by the control unit 253, it will be displayed on the display 251 of the mainframe control system 25. On the basis of the data displayed, the operator can determine whether to continue the treatment. If the treatment needs to be stopped, manipulate a operation knob 252 to stop the treatment.

The invention claimed is:

1. An ultrasound treatment clamp comprising two handles and two ultrasound therapy applicators,
wherein:
the two handles are scissor-like clamp-shaped, and comprise a holding part and a clamp part,
each handle is connected to one of the two ultrasound therapy applicators,
the two handles are connected by a pin, the holding parts of the handles are arranged proximal to the pin, and the clamp parts of the handles are arranged distal to the pin,
two connection tubes are arranged between the two ultrasound therapy applicators and the two clamps parts, with each connection tube being connected to one of the two ultrasound therapy applicators at one end and connected to the clamp part of the clamp-shaped handle at the other end,
the two ultrasound therapy applicators having central axes overlapping each other are mounted face to face,
a parallel moving mechanism configured to keep the two ultrasound therapy applicators in parallel when moving along with the clamps is connected between the connection tubes connected to the two clamps.

2. The ultrasound treatment clamp as claimed in claim 1, wherein:
each connection tube is connected to the clamp of the clamp-shaped handle through a joint,
the connection tubes comprise passages for fluid and electrical signals at the connection of the connection tubes and the joint, and the passages for fluid and electrical signals are connected to the ultrasound therapy applicator.

3. The ultrasound treatment clamp as claimed in claim 1, wherein:
   each connection tube is connected to the ultrasound therapy applicator by a rotating joint, and
   the ultrasound therapy applicator rotates freely on the rotating joint to focus the ultrasound transversely or longitudinally.

4. The ultrasound treatment clamp as claimed in claim 1, wherein:
   the parallel moving mechanism comprises a telescopic mechanism in a parallelogram formed by a plurality of link blocks hinged with each other,
   a sliding sleeve on the connection tube slides back and forth,
   the link block at one corner of outer end of the parallel moving mechanism is hinged with the sliding sleeve, and
   the link block at the other corner of outer end of the parallel moving mechanism is fixed on the clamp.

5. The ultrasound treatment clamp as claimed in claim 1, wherein:
   the parallel moving mechanism is telescopic pipe components comprising big hollow pipes and small hollow pipes which are encased in the big hollow pipes and can extend and slide.

6. The ultrasound treatment clamp of any one of claim 1, 2, 3, 4 or 5, characterized in that each of the two said ultrasound therapy applicators comprise:
   an ultrasound transducer; and
   a fluid container to accommodate fluid,
   wherein, in each of the two ultrasound therapy applicators, the ultrasound transducer is placed in the fluid container and an acoustic transparent membrane is fixed at the open part of the container by an airtight device.

7. The ultrasound treatment clamp as claimed in claim 6, characterized in that said fluid is degassed water.

8. The ultrasound treatment clamp as claimed in claim 6, characterized in that each of the two ultrasound transducers is a focusing or a non-focusing ultrasound transducer.

9. The ultrasound treatment clamp as claimed in claim 6, characterized in that a bracket is provided in said each fluid container and each of the two ultrasound transducers are placed on the bracket.

10. The ultrasound treatment clamp as claimed in claim 9, characterized in that a focal distance adjusting device is provided on at least one of the fluid containers, one end of said focal distance adjusting device extending into the fluid container is connected to the bracket.

11. The ultrasound treatment clamp as claimed in claim 10, characterized in that said focal distance adjusting device includes a screw connected to the bracket, a seal ring and a seal nut covered on the screw, an adjusting knob on the seal nut and a fixing bolt on the adjusting knob, the seal ring clings to the outside wall of the fluid container.

12. The ultrasound treatment clamp as claimed in claim 6, characterized in that a slot for mounting an ultrasound therapy guiding assembly is provided on at least one of each of the two ultrasound transducers.

13. The ultrasound treatment clamp as claimed in claim 12, characterized in that said ultrasound therapy guiding assembly is a semiconductor lighting device or a B-mode ultrasound probe.

14. The ultrasound treatment clamp as claimed in claim 6, characterized in that each of said two ultrasound therapy applicators further comprise a temperature sensor fixed on a side of each of the said two ultrasound therapy applicators that is opposite a side of each of the ultrasound transducer.

15. The ultrasound treatment clamp as claimed in claim 6, characterized in that a locker for fixing the position of handles is provided between the two handles.

* * * * *